United States Patent [19]

Mazour

[11] 4,287,136
[45] Sep. 1, 1981

[54] PROCESS FOR THE PREPARATION OF O,O-DIALKYLTHIONOPHOSPHORIC ACID CHLORIDES

[75] Inventor: Zdenek Mazour, Lausen, Switzerland

[73] Assignee: Ciba-Geigy Corporation, Ardsley, N.Y.

[21] Appl. No.: 159,884

[22] Filed: Jun. 16, 1980

[51] Int. Cl.³ ............................................... C07F 9/20
[52] U.S. Cl. .................................................. 260/985
[58] Field of Search ...................................... 260/985

[56] References Cited

PUBLICATIONS

Bentrude, et al., "J. Am. Chem. Soci.," vol. 95, (1973), p. 2292.

*Primary Examiner*—Anton H. Sutto
*Attorney, Agent, or Firm*—Karl F. Jorda

[57] ABSTRACT

Preparation of O,O-dialkylthionophosphoric acid chlorides of the formula

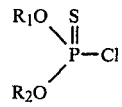

in which $R_1$ and $R_2$ independently of one another are each an alkyl group having 1–6 carbon atoms, by reacting a dialkyl phosphite-chloride of the formula

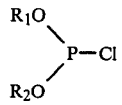

with sulfur in an inert solvent in the presence of a catalytic amount of titanium tetrachloride.

The O,O-dialkylthionophosphoric acid chlorides of the above formula are valuable intermediates for the preparation of insecticidal active compounds.

14 Claims, No Drawings

PROCESS FOR THE PREPARATION OF O,O-DIALKYLTHIONOPHOSPHORIC ACID CHLORIDES

The present invention relates to a process for the preparation of O,O-dialkylthionophosphoric acid chlorides of the formula I

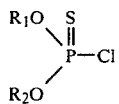     (I)

in which $R_1$ and $R_2$ independently of one another are each an alkyl group having 1–6 carbon atoms, by reacting a dialkyl phosphite-chloride of the formula II

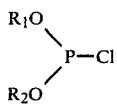     (II)

in which $R_1$ and $R_2$ are as defined above, with sulfur.

The O,O-dialkylthionophosphoric acid chlorides of the formula I are valuable intermediates for the preparation of insecticidal active compounds. Active compounds of this type and their preparation and use are described, for example, in U.S. Patent Nos. 2,754,243 and 3,992,533.

It is known to prepare O,O-dialkylthionophosphoric acid chlorides by reacting dialkyl phosphite-chlorides with sulfur in an inert solvent. However, this reaction leads to usable results only in the case of bis-($\beta$-chloroethyl) phosphite-chlorides (cf. U.S. Pat. No. 2,536,647). The reaction of dialkyl phosphite-chlorides proceeds under the same conditions only with a low conversion and with the formation of a large amount of by-products. Thus, for example, when diethyl phosphite-chloride is reacted, the conversion achieved after a reaction time of 12 hours is only 33%, and 10 to 25% of by-products are formed.

It is also known to carry out the reaction of dialkyl phosphite-chlorides with sulfur in the presence of aluminium chloride as a catalyst. In J. Amer. Chem. Soc. 95, 2292 (1973) a yield of O,O-diethylthionophosphoric acid chloride of 80% of theory is indeed described for the reaction of diethyl phosphite-chloride with the equivalent amount of sulfur in the presence of the equimolar amount of aluminium chloride, but, according to analysis by gas chromatography, this product consists only to the extent of 60% of O,O-diethylthionophosphoric acid chloride. It follows from this that the desired product is formed only in a yield of about 50% of theory. These results show that when aluminium chloride is used as the catalyst the reaction is indeed accelerated, but the selectivity further decreases.

With the methods known hitherto it is not possible to prepare the O,O-dialkylthionophosphoric acid chlorides of the formula I in a simple and economical manner. The disadvantage of the known methods lies, in particular, in the fact that mixtures of substances are always obtained in which unconverted starting material and by-products are present in addition to the desired O,O-dialkylthionophosphoric acid chloride; the separation of these substances is involved.

It is, therefore, the object of the present invention to provide a process by which the O,O-dialkylthionophosphoric acid chlorides can be obtained in a pure form in a simple and economical manner.

According to the present invention it is proposed to carry out the reaction of dialkyl phosphite-chlorides of the formula II with sulfur in an inert solvent in the presence of a catalytic amount of titanium tetrachloride.

Suitable inert solvents in which the reaction of dialkyl phosphite-chlorides of the formula II with sulfur can be carried out, are aliphatic, cycloaliphatic, aromatic and halogenated hydrocarbons. Examples of suitable inert solvents are petroleum ether, pentane, hexane, heptane, ligroin, benzene, toluene, xylene, methylene chloride, chloroform, carbon tetrachloride, 1,2-dichloroethane, tetrachloroethane and chlorobenzene. Preferred solvents are benzene, toluene and xylene.

The reaction temperature at which the reaction of a dialkyl phosphite-chloride of the formula II with sulfur is carried out is as a rule between 0° C. and the reflux temperature of the reaction medium. Preferably, the reaction of a dialkyl phosphite-chloride of the formula II with sulfur is carried out at a temperature of 20°–120° C. and in particular at 40°–100° C.

The dialkyl phosphite-chlorides of the formula II and sulfur are as a rule employed in equivalent amounts, but either the one or the other component can be present in a slight excess. In particular, it is advantageous to use a slight excess of sulfur. Preferably, therefore, 1.0–1.1 grams atoms of sulfur are used per mol of dialkyl phosphite-chloride of the formula II.

According to the invention, the titanium tetrachloride can be used in an amount of 0.005–0.1 mol per mol of dialkyl phosphite-chloride of the formula II. Preferably, 0.01–0.05 mol of titanium tetrachloride are used per mol of dialkyl phosphite-chloride of the formula II. The use of 0.02–0.03 mol of titanium tetrachloride per mol of dialkyl phosphite-chloride of the formula II is particularly preferred.

The alkyl radicals $R_1$ and $R_2$ having 1–6 carbon atoms can be straight-chain or branched and specifically are methyl, ethyl, propyl, isopropyl, butyl, isobutyl, sec.-butyl, tert.-butyl, pentyl, neopentyl (2,2-dimethylpropyl) or hexyl. Preferably, the radicals $R_1$ and $R_2$ independently of one another are each an alkyl group having 2–4 carbon atoms. A particularly preferred dialkyl phosphite-chloride of the formula II is diethyl phosphite-chloride.

According to a preferred embodiment of the process according to the invention, a dialkyl phosphite-chloride of the formula II, in which $R_1$ and $R_2$ independently of one another are each an alkyl group having 2 to 4 carbon atoms, is reacted at 40°–100° C. in the presence of 0.02 to 0.03 mol of titanium tetrachloride per mol of dialkyl phosphite-chloride of the formula II, in benzene, toluene or xylene as the solvent, with 1.0 to 1.1 gram atoms of sulfur per mol of dialkyl phosphite-chloride of the formula II.

The process according to the invention is as a rule carried out under normal pressure. It can, however, also be carried out under elevated or reduced pressure, if particular circumstances make this necessary.

By means of the process according to the invention it is possible to prepare O,O-dialkylthionophosphoric acid chlorides of the formula I in a simple and economical manner. The process is particularly suitable for the preparation of O,O-dialkylthionophosphoric acid chlorides of the formula I on an industrial scale. It can be carried out either discontinuously or continuously. A particular advantage of the process according to the invention lies in the fact that the O,O-dialkylthionophosphoric acid chlorides of the formula I are formed with a selectivity of more than 90%, with virtually complete conversion of the dialkyl phosphite-chlorides of the formula II. A further essential advantage of the process according to the invention is that the titanium tetrachloride used as the catalyst is required in only a very small amount, whilst in the known process mentioned initially aluminium chloride has to be used in an equimolar amount. As a result of the high selectivity, the process according to the invention yields a crude product which is already relatively pure and in many cases can be used direct for further reactions. If required, however, the crude product can be brought to the desired degree of purity in a simple manner by rectification.

The process according to the invention is illustrated in more detail by the examples which follow.

EXAMPLE 1

Preparation of O,O-diethylthionophosphoric acid chloride using aluminium chloride as the catalyst (known process).

A solution of 15.97 g (0.1 mol) of diethyl phosphite-chloride (98%) is added dropwise in the course of 30 minutes to a suspension of 3.2 g (0.1 gram atom) of sulfur and 13.0 g (0.1 mol) of aluminium chloride in 200 ml of benzene, at 0° C., with stirring and under nitrogen. After all of the diethyl phosphite-chloride has been added, the reaction mixture is stirred for 14 hours at the reflux temperature. It is then cooled and filtered and the benzene is distilled off in vacuo. 16.02 g (85% of theory) of crude O,O-diethylthionophosphoric acid chloride are obtained as the residue, but, according to analysis by gas chromatography and mass spectroscopy, this product consists only to the extent of 60% of O,O-diethylthionophosphoric acid chloride. The remainder consists in the main of O,O,O-triethyl thiophosphate and O-ethyl dichlorothiophosphate. Separating off these by-products by distillation is possible only with a great deal of effort.

EXAMPLE 2

Preparation of O,O-diethylthionophosphoric acid chloride by the process according to the invention 2.5 ml (4.31 g; 0.023 mol) of titanium tetrachloride are introduced into a solution of 159.7 g (1.0 mol) of diethyl phosphite-chloride (98%) in 150 ml of toluene, with stirring and under nitrogen. The resulting solution is then warmed to 80° C., and 33.6 g (1.05 gram atoms) of sulfur are introduced in portions in the course of 30 minutes. A clear, yellowish solution forms and after the addition of the sulfur this is stirred for a further 6 hours at 80° C. After this reaction time, the conversion, according to analysis by gas chromatography, is 93% of the diethyl phosphite-chloride employed. After cooling the reaction mixture to 0°–5° C., separating off the unreacted sulfur by filtration and distilling off the toluene in vacuo, 175.3 g of crude product are obtained; according to analysis by gas chromatography, this product consists to the extent of 91.4% of O,O-diethylthionophosphoric acid chloride. This corresponds to a yield of O,O-diethylthionophosphoric acid chloride of 85% of theory, based on diethyl phosphite-chloride employed.

EXAMPLE 3

Preparation of O,O-di-n-butylthionophosphoric acid chloride by the process according to the invention 0.5 ml (0.86 g; 0.0045 mol) of titanium tetrachloride are introduced into a solution of 44.2 g (0.2 mol) of di-n-butyl phosphite-chloride (96.1%) in 30 ml of toluene, with stirring and under nitrogen, at 22° C. 6.7 g (0.21 gram atom) of sulfur are introduced in portions in the course of 30 minutes into the solution, which has been warmed to 90° C. The clear, yellowish solution obtained after adding the sulfur is stirred for a further 20 hours at 90° C. The reaction mixture is then cooled to 0°–5° C., the unreacted sulfur is separated off by filtration and the toluene is distilled off in vacuo. This yields 49.0 g of crude product which, according to analysis by gas chromatography, consists to the extent of 89.2% of di-n-butylthionophosphoric acid chloride. This corresponds to a yield of 89.4% of theory, based on di-n-butyl phosphite-chloride employed.

What is claimed is:

1. A process for the preparation of an O,O-dialkylthionophosphoric acid chloride of the formula I

(I)

in which $R_1$ and $R_2$ independently of one another are each an alkyl group having 1–6 carbon atoms, by reacting a dialkyl phosphite-chloride of the formula II

(II)

in which $R_1$ and $R_2$ are as defined above, with sulfur, which comprises carrying out the reaction of the dialkyl phosphite-chloride of the formula II with sulfur in an inert solvent in the presence of a catalytic amount of titanium tetrachloride.

2. A process according to claim 1, wherein the inert solvent used is an aliphatic, cycloaliphatic, aromatic or halogenated hydrocarbon.

3. A process according to claim 1, wherein the inert solvent used is pentane, hexane, heptane, ligroin, benzene, toluene, xylene, methylene chloride, chloroform, carbon tetrachloride, 1,2-dichloroethane, tetrachloroethane or chlorobenzene.

4. A process according to claim 1, wherein the inert solvent used is benzene, toluene or xylene.

5. A process according to claim 1, wherein the reaction of a dialkyl phosphite-chloride of the formula II with sulfur is carried out at a temperature between 0° C. and the reflux temperature of the reaction medium.

6. A process according to claim 1, wherein the reaction of a dialkyl phosphite-chloride of the formula II with sulfur is carried out at a temperature of 20° to 120° C.

7. A process according to claim 1, wherein the reaction of a dialkyl phosphite-chloride of the formula II with sulfur is carried out at a temperature of 40° to 100° C.

8. A process according to claim 1, wherein 1.0 to 1.1 gram atoms of sulfur are used per mol of dialkyl phosphite-chloride of the formula II.

9. A process according to claim 1, wherein the titanium tetrachloride is used in an amount of 0.005 to 0.01 mol per mol of dialkyl phosphite-chloride of the formula II.

10. A process according to claim 1, wherein the titanium tetrachloride is used in an amount of 0.01 to 0.05 mol per mol of dialkyl phosphite-chloride of the formula II.

11. A process according to claim 1, wherein the titanium tetrachloride is used in an amount of 0.02 to 0.03 mol per mol of dialkyl phosphite-chloride of the formula II.

12. A process according to claim 1, wherein a dialkyl phosphite-chloride of the formula II is used in which the radicals $R_1$ and $R_2$ independently of one another are each an alkyl group having 2 to 4 carbon atoms.

13. A process according to claim 1, wherein the dialkyl phosphite-chloride of the formula II which is used is diethyl phosphite-chloride.

14. A process according to claim 1, wherein a dialkyl phosphite-chloride of the formula II, in which the radicals $R_1$ and $R_2$ independently of one another are each an alkyl group having 2 to 4 carbon atoms, is reacted at 40°–100° C. in the presence of 0.02 to 0.03 mol of titanium tetrachloride per mol of dialkyl phosphite-chloride of the formula II, in benzene, toluene or xylene as the solvent, with 1.0 to 1.1 gram atoms of sulfur per mol of dialkyl phosphite-chloride of the formula II.

* * * * *